United States Patent [19]

Tachikawa et al.

[11] 4,022,832
[45] May 10, 1977

[54] 2-AMINOACETAMIDO-α-PHENYLBEN-ZYLIDENEAMINOALKANOL DERIVATIVES AND PROCESS FOR THE PREPARATION THEREOF

[75] Inventors: Ryuji Tachikawa; Tetsuo Miyadera; Atsusuke Terada; Toshiharu Kamioka; Syunji Naruto, all of Tokyo, Japan

[73] Assignee: Sankyo Company Limited, Tokyo, Japan

[22] Filed: Dec. 31, 1975

[21] Appl. No.: 645,890

[30] Foreign Application Priority Data

Jan. 20, 1975 Japan .................................. 50-8503

[52] U.S. Cl. ...................... 260/562 N; 260/566 R; 424/324
[51] Int. Cl.² ...................................... C07C 103/50
[58] Field of Search ................................ 260/562 N

[56] References Cited

UNITED STATES PATENTS

| | | | |
|---|---|---|---|
| 3,136,815 | 6/1964 | Reeder et al. | 260/562 N |
| 3,202,699 | 8/1965 | Stempel | 260/562 N |
| 3,657,344 | 4/1972 | Stempel et al. | 260/562 N |
| 3,755,300 | 8/1973 | Tachikawa | 260/562 N |

FOREIGN PATENTS OR APPLICATIONS 1,212,105   3/1966   Germany

*Primary Examiner*—Arthur P. Demers
*Attorney, Agent, or Firm*—Flynn & Frishauf

[57] ABSTRACT

Aminoalkanol derivatives having the formula

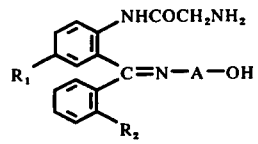

wherein $R_1$ represents hydrogen atoms or a halogen atom, $R_2$ represents hydrogen atom or fluorine atom and A represents an alkylene group having 1–4 carbon atoms. The aminoalkanol derivatives are useful as a minor tranquilizer and can be prepared by reacting the corresponding 2-amino-α-phenylbenzylideneaminoalkanol derivative with an aminocarboxylic acid.

6 Claims, No Drawings

2-AMINOACETAMIDO-α-PHENYLBEN-ZYLIDENEAMINOALKANOL DERIVATIVES AND PROCESS FOR THE PREPARATION THEREOF

This invention relates to novel aminoalkanol derivatives and a process for the preparation thereof.

More particularly it relates to novel aminoalkanol derivatives having the formula

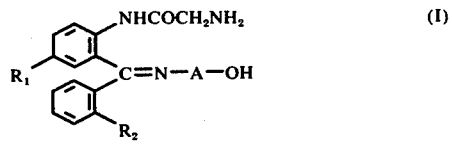

wherein $R_1$ represents hydrogen atom or a halogen atom, $R_2$ represents hydrogen atom or fluorine atom and A represents an alkylene group having 1-4 carbon atoms and a process for the preparation thereof.

In the above formula (I), the halogen atom may be fluorine, chlorine or bromine. The alkylene group may be a straight or branched alkylene group having 1-4 carbon atoms, for example, methylene, ethylene, trimethylene, 1-methylethylene, 2-methylethylene, tetramethylene, 1,2-butylene, 1,3-butylene or 2,3-butylene.

The aminoalkanol derivatives of the above formula (I) are all novel compounds unknown in the prior art. They possess a depressing activity on the central nervous system and useful as a minor tranquilizer.

The aminoalkanol derivatives having the formula (I) can be administered orally or parenterally in any of the usual pharmaceutical forms including tablets, capsules, powders, suspensions, solutions and syrups. The dosage unit depends upon conditions of the symptoms to be treated, the age and body weight of patients. A usual unit is in amounts from 0.05 to 10 mg/kg of body weight/day for adults and may be administered once or separately several times a day.

According to the process of this invention, the aminoalkanol derivative having the formula (I) can be prepared by reacting a compound having the formula

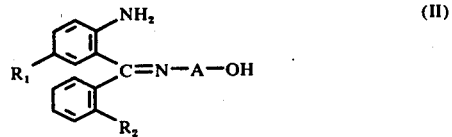

wherein $R_1$, $R_2$ and A are the same as defined above with an aminocarboxylic acid having the formula

wherein Z represents hydrogen atom or a protective group for amino group or a reactive derivative thereof to give a compound having the formula

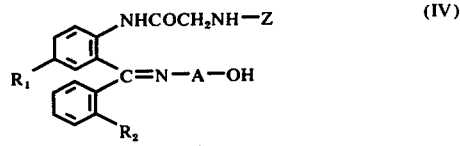

wherein $R_1$, $R_2$, A and Z are the same as defined above and, when Z is a protecting group for amino group, subjecting the latter compound to hydrolysis.

In the above formulae (III) and (IV), the protecting group for amino group may be a group which can be easily removed by hydrolysis, preferably a halogenoacetyl group, e.g., dichloroacetyl, dibromoacetyl, trichloroacetyl, tribromoacetyl and trifluoroacetyl.

The reaction of the compound (II) with the aminocarboxylic acid (III) or the reactive derivative thereof may be carried out in the presence or absence of a solvent.

In case where the aminocarboxylic acid (III) is used as the reactant, it is necessary to employ a condensing agent as follows;

N,N'-disubstituted carbodiimide such as N,N'-dicyclohexylcarbodiimide, 1-(3-dimethylaminopropyl)-3-ethylcarbodiimide hydrochloride, 1-cyclohexyl-3-(2-morpholinoethyl)-carbodiimide or 1-cyclohexyl-3-(N-methyl-2-morpholiniumethyl)carbodiimide; a disubstituted carbonyl compound such as N,N'-carbonyldiimidazole, di-α-pyridylcarbonate, S,S'-carbonyldi(α-thiopyridine), N,N'-carbonyldi(1,2,4-triazolide), N,N'-carbonyldi(1,2,3-triazolide), N,N'-carbonyldi(1,2,3,5-tetrazolide) or N,N'-carbonyldi(3,5-dimethylpyrazolide); a chlorocarbonic acid ester such as methyl chlorocarbonate, ethyl chlorocarbonate or isobutyl chlorocarbonate; a disubstituted thionyl compound such as N,N'-thionyldiimidazole, di-p-nitrophenyl sulfite or di-p-nitrophenyl thiosulfite; a phosphoric acid compound such as tri-p-nitrophenyl phosphate, diimidazole-1-phosphinic acid monoester, diethyl chlorophosphite, or tetraethyl pyrophosphite; Woodward's reagent such as N-ethyl-5-phenylisoxazolium-3'-sulfonic acid salt; an acetylenic compound such as ethoxyacetylene, methylethynyl diethylamine, ethylethynyl diethylamine, propylethynyl diethylamine or butylethynyl diethylamine; a nitrogen compound such as trichloroacetonitrile, N,N-diethylcyanamide, N,N-diphenylcyanamide, N,N-dibenzylcyanamide or diphenylketene-p-tolylimine; a trifluoroacetic acid ester such as p-nitrophenyl trifluoroacetate or pentachlorophenyl trifluroacetate; an arylsulfonyl chloride such as phenylsulfonyl chloride; an unsaturated heterocyclic compound such as dihydropyrane; a N-carbonylamino acid ester such as ethyl N-carbonylglycinate; a ketene such as diphenylketene; an oxime such as 3-nitroacetophenone oxime; an N-acyloxazolidinone such as N-benzyloxycarbonyloxazolidinone or N-tosyloxazolidinone; a trivalent phosphorus compound-disulfide compound such as triphenylphosphine-2,2'-dipyridylsulfide or triphenylphosphite-2,2'-dipridylsulfide; a phosphazo compound.

However, the condensing agents are not particularly limited to those cited above. The generally known methods for the preparation of acid amides can be employed as well in the process of this invention.

Depending upon the sort of the condensing agent utilized, for instance, where the phosphoric acid compound is employed as a condensing agent, the reaction may be preferably carried out in the presence of an organic base such a heterocyclic compound as pyridine, picoline, lutidine, quinoline, isoquinoline, collidine, N-methylpiperidine or N-methylmorpholine and such a tertiary amine as triethylamine or tri-n-butylamine; and an inorganic base such a carbonate of alkali or alkaline earth metal as sodium carbonate, potassium carbonate or calcium carbonate, such a hydroxide of alkali or alkaline earth metal as sodium hydroxide, potassium hydroxide or calcium hyroxide, and such a hydrogen carbonate of alkali or alkaline earth metal as sodium hydrogen carbonate, potassium hydrogen carbonate or calcium hydrogen carbonate. And when the condensing agent employed is, for instance, N,N'-disubstituted carbodiimide such as N,N'-dicyclohexylcarbodiimide, the aminocarboxylic acid (III) is preferably used in the form of salt such as, for instance, hydrochloride, sulfate or nitrate.

As the reactive derivative of the aminocarboxylic acid (III), there may be employed the halide, e.g., the chloride or bromide; the mixed anhydride with phenylacetic acid; the azide, the alkyl or aryl ester, e.g., the methyl, ethyl or p-nitrophenyl ester; the mixed acid imide with acetamide or propionamide. However, the reactive derivative of the aminocarboxylic acid (III) is not particularly limited to those exemplified above.

In case where the halide or azide of the aminocarboxylic acid is employed, the reaction may be preferably carried out in the presence of an organic or inorganic base. As the organic base, there may be employed a heterocyclic amine, e.g., pyridine, picoline, lutidine, quinoline, isoquinoline, collidine, N-methylpiperidine or N-methylmorpholine and a tertiary amine, e.g., triethylamine or tri-n-butylamine. As the inorganic base, there may be employed a carbonate of alkali or alkaline earth metal, e.g., sodium carbonate, potassium carbonate or calcium carbonate, a hydroxide of alkali or alkaline earth metal, e.g., sodium hydroxide, potassium hydroxide or calcium hydroxide and a hydrogen carbonate of alkali or alkaline earth metal, e.g., sodium carbonate, potassium hydrogen carbonate or calcium hydrogen carbonate. However, the base employed is not particularly limited to those cited above. The organic base may also surve as a solvent in the reaction.

In operating the process of this invention, the reaction is carried out in the presence or absence of the solvent, but it is preferable to use a solvent for the reaction to proceed smoothly. As to the solvent which may be employed in the reaction, there is no particular limitation unless it would participate in the reaction. As examples of such a solvent are mentioned a lower alkanol such as methanol, ethanol or isopropanol; an ether such as diethyl ether, tetrahydrofuran or dioxane; a halogenated hydrocarbon such as chloroform, dichloromethane or dichloroethane; an aromatic hydrocarbon such as benzene, toluene or xylene; a lower carboxylic acid ester such as ethyl acetate or methyl propionate; a nitrile such as acetonitrile; a dialkylformamide such as dimethylformamide; a dialkylsulfoxide such as dimethylsulfoxide; a heterocyclic compound such as pyridine, picoline, lutidine, quinoline, isoquinoline, collidine, N-methylpiperidine or N-methylmorpholine; a tertiary amine such as triethylamine or tri-n-butylamine, and the like. As particularly preferable solvents may be mentioned, for instance, benzene, tetrahydrofuran, dioxane, acetonitrile, dichloromethane and dimethylformamide.

The reaction temperature is not particularly critical, but it is desirable to perform the reaction at a relatively low temperature in order to suppress for the adverse reaction to occur. Usually the reaction is carried out preferably under ice-cooling at the first stage of the reaction and then the temperature is raised gradually to room temperature.

When the reactive derivative of the carboxylic acid having the general formula (III) is an ester, the reaction does not proceed sufficiently below room temperature and therefore is usually carried out preferably on heating. The time required for the reaction may be varied mainly depending upon the sort of starting material, the presence or absence and sort of the solvent, the reaction temperature employed and the like.

The reaction product can be recovered from the reaction mixture by a usual manner. For example, after the reaction is completed, an appropriate amount of water or aqueous sodium chloride solution is added to the reaction mixture, which is then extracted with a suitable organic solvent, the organic layer washed with water and dried, and the solvent is removed by distillation to afford the desired product. The conventional purification techniques such as recrystallization or column chromatography may be applied further in order to obtain a pure substance.

When the substituent represented by Z in the compounds having the formula (IV) is a protecting group of amino group such as dichloroacetyl, trichloroacetyl or trifluoroacetyl group, the hydrolysis reaction for removing such a protecting group is carried out by a usual manner using a hydrolysis reagent in the presence of water. As examples of a hydrolysis reagent may be mentioned an alkaline reagent such an alkali metal hydroxide as sodium hydroxide or potassium hydroxide, such an alkaline earth metal hydroxide as calcium hydroxide or barium hydroxide, such an alkali metal carbonate as sodium carbonate or potassium carbonate, such an alkali metal hydrogen carbonate as sodium hydrogen carbonate or potassium hydrogen carbonate, and such as ammonium hydroxide or the like. But an alkali metal carbonate such as sodium carbonate or potassium carbonate is used preferably. Usually the reaction is carried out preferably in the presence of a solvent, and as the solvents which are preferably employed may be mentioned, for instance, water; an alkanol such as methanol, ethanol or n-propanol; an ether such as tetrahydrofuran or dioxane; a dialkylformamide such as dimethylformamide. Particularly preferable is a mixture of water and an organic solvent. As to the reaction temperature there is not any critical limitation, but it is desirable to carry out the reaction at a relatively low temperature in order to suppress for the adverse reaction to occur, and preferably near at room temperature. The time required for the reaction may be varied mainly depending upon the sort of the starting material and solvent, the reaction temperature employed and the like, but it may usually take about 8 to 20 hours.

After the reaction is completed, the desired product having the general formula (I) can be recovered from the reaction mixture by a usual manner: For example, the solvent is removed from the reaction mixture, the residue extracted with a suitable organic solvent, the extract washed with water, dried, and the solvent is evaporated from the extract to leave the desired product, which may be purified, if necessary, by a conventional techniques such as recrystallization and column chromatography.

The following examples are presented to further illustrate the present invention.

EXAMPLE 1

2-{[2-Aminoacetamido-5-bromo-α-(2-fluorophenyl)-benzylidene]amino}ethanol

To a solution of 4.5g of N,N'-dicyclohexylcarbodiimide in 100ml of dimethylformamide is added a solution of 2.2g of glycine hydrochloride in 2.2ml of water in a period of about 30 seconds under stirring and ice-cooling. Immediately a solution of 3.4g of 2-{[2-amino-5-bromo-α-(2-fluorophenyl)benzylidine]amino-}ethanol in 10ml of tetrahydrofuran is added dropwise to the reaction mixture, and the mixture is stirred for further 3 hours at room temperature. After completion of the reaction, one liter of water is added to the reaction mixture which is extracted once with 100ml and four times with 50ml of benzene. The organic layer is washed with water, dried over anhydrous sodium sulfate, and the solvent is distilled off to give an oily substance, which is purified by chromatography of alumina column and then recrystallized from benzene-n-hexane (3:2 in volume) mixture yielding 2.3g of the desired product melting at 167°–168° C.

EXAMPLE 2

2-[(2-Aminoacetamido-5-bromo-α-phenylbenzylidene)-amino]ethanol

To a solution of 3.2g of 2-(2-amino-5-bromo-α-phenylbenzylideneamino)ethanol and 2.6g of trichloroacetylglycine in 50ml of dichloromethane is added 2.5g of N,N'-dicyclohexylcarbodiimide at 0° C, the temperature of the mixture is then raised gradually to room temperature and stirring is continued for 3 hours. After completion of the reaction, the precipitates formed in the reaction mixture is removed by filtration, and the solvent is evaporated from the filtrate to give 4.3g of a crystalline substance melting at 175°–176° C. The crystals are dissolved in a mixture of 80ml of methanol and 80ml of tetrahydrofuran, a solution of 4.0g of sodium carbonate in 80ml of water is added to this solution, and the mixture is stirred at room temperature overnight. After completion of the reaction, the solvent is evaporated from the reaction mixture, the residue extracted with dichloromethane, the extract washed with water, dried over anhydrous sodium sulfate, and the solvent is removed by distillation to give the desired product, which is recrystallized from ethyl acetate affording 0.96g of the desired product melting at 153°–154° C.

EXAMPLE 3

2-{[2-Aminoacetamido-5-chloro-α-(2-fluorophenyl)-benzylidene]amino}ethanol

To a solution of 4.5g of N,N'-dicyclohexylcarbodiimide in 100ml of dimethylformamide is added a solution of 2.2g of glycine hydrochloride in 2.2ml of water in a period of about 30 seconds under stirring and ice-cooling. Immediately a solution of 3.2g of 2-{[2-amino-5-chloro-α-(2-fluorophenyl)benzylidene]-amino}ethanol in 10ml of tetrahydrofuran is added dropwise to the above solution and the mixture stirred for further 3 hours. After completion of the reaction, the reaction mixture is treated by the same manner as described in the Example 1, yielding 1.7g of the desired product melting at 128°–132° C.

EXAMPLE 4

2-[(2-Aminoacetamido-5-chloro-α-phenylbenzylidene) amino]propanol

To a solution of 4.5g of N,N'-dicyclohexylcarbodimide in 100ml of dimethylformamide is added a solution of 2.2g of glycine hydrochloride in 2.2ml of water in a period of about 30 seconds under stirring and ice-cooling. To the reaction mixture is immediately added dropwise a solution of 3.3g of 2-[(2-amino-5-chloro-α-phenylbenzylidene)amino]propanol in 10ml of tetrahydrofuran and the mixture is stirred for further 3 hours at room temperatures. After the reaction is completed, the reaction mixture is treated by the same manner as described in the Example 1 to give 1.3g of the desired product melting at 168°–172° C.

The pharmacological activities of the compounds which are prepared according to the process of this invention are shown below with $ED_{50}$ values obtained, together with the test methods using mice as experimental animals.

Test Methods

1. Anti-bemegride convulsant effect

One hour after oral adminitration of the test compound, 30mg/kg of bemegride is subcutaneously injected and the anti-convulsant activity of the compound is observed for 30 minutes.

2. Anti-electroshock convulsant effect

One hour after oral administration of the test compound, an electroshock (1000V, 12.5mA, 0.2sec.) is applied through both corneas and anti-convulsant activity of the compound is observed.

3. Potentiation of anesthesia

One hour after oral administration of the test compound, 30mg/kg of thiopental is intravenously injected, and the dose is determined which prolongs the duration of loss of the righting reflex twice that of the group administered only with thiopental.

4. Calculation of $ED_{50}$ values

The values are calculated according to the method of Litchfield and Wilcoxon [J. Pharmcol. Exp. Therap., 96, 99(1949)].

| Pharmacological activities | | $ED_{50}$ | (mg/kg; P.O.) |
|---|---|---|---|
| Compound \ Activities | Anti-bemegride convulsant | Anti-electroshock convulsant | Anesthesia potentiation |
| 2- [2-Amionacetamido-5-bromo-α-(2-fluorophenyl) benzylidene]amino - ethanol | 0.31 | 8.0 | 2.9 |
| Chlordiazepoxide | 2.7 | 27 | 12 |

What is claimed is:

1. A compound having the formula

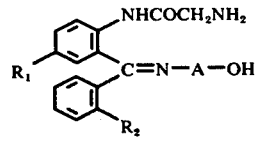

wherein $R_1$ represents hydrogen atom or a halogen atom, $R_2$ represents hydrogen atom or fluorine atom and A represents an alkylene group having 1–4 carbon atoms.

2. A compound of claim 1 wherein $R_1$ is chlorine or bromine and A is ethylene or trimethylene.

3. A compound of claim 1 wherein $R_1$ is bromine, $R_2$ is fluorine and A is ethylene.

4. A compound of claim 1 wherein $R_1$ is bromine, $R_2$ is hydrogen and A is ethylene.

5. A compound of claim 1 wherein $R_1$ is chlorine, $R_2$ is fluorine and A is ethylene.

6. A compound of claim 1 wherein $R_1$ is chlorine, $R_2$ is hydrogen and A is trimethylene.

* * * * *